United States Patent [19]

Beastall et al.

[11] Patent Number: 5,087,239
[45] Date of Patent: Feb. 11, 1992

[54] TAMPON APPLICATOR

[75] Inventors: Alan L. Beastall, Havant; Malcolm G. Guest, Drayton, both of United Kingdom

[73] Assignee: Tampax Limited, United Kingdom

[21] Appl. No.: 631,205

[22] Filed: Dec. 21, 1990

Related U.S. Application Data

[60] Division of Ser. No. 484,434, Feb. 16, 1990, abandoned, which is a continuation of Ser. No. 563,977, Dec. 21, 1983, abandoned.

[30] Foreign Application Priority Data

Dec. 23, 1982 [GB] United Kingdom ............ 8236603

[51] Int. Cl.$^5$ .............................................. A61F 13/20
[52] U.S. Cl. ................................................ 604/14
[58] Field of Search ............... 604/14, 15, 11; 206/529, 530, 438

[56] References Cited

U.S. PATENT DOCUMENTS

| | | | |
|---|---|---|---|
| 3,204,635 | 9/1965 | Voss et al. | 128/263 |
| 3,760,808 | 9/1973 | Bleuer | 604/14 |
| 3,895,634 | 7/1975 | Berger et al. | 604/14 |
| 4,412,833 | 11/1983 | Wiegner et al. | 604/14 |
| 4,453,925 | 6/1984 | Decker | 604/14 |
| 4,479,791 | 10/1984 | Sprague | 604/14 |
| 4,508,531 | 4/1985 | Whitehead | 604/14 |

FOREIGN PATENT DOCUMENTS

| | | |
|---|---|---|
| 6213580 | 9/1980 | Australia . |
| 52-30800 | 7/1977 | Japan . |
| 52-131898 | 10/1977 | Japan . |
| 55-23619 | 6/1980 | Japan . |
| 55-125321 | 9/1980 | Japan . |
| 55-155647 | 12/1980 | Japan . |
| 55-155648 | 12/1980 | Japan . |
| 55-166149 | 12/1980 | Japan . |
| 55-171028 | 12/1980 | Japan . |
| 58-9129 | 7/1981 | Japan . |
| 56-31221 | 7/1981 | Japan . |
| 56-51853 | 12/1981 | Japan . |
| 57-4258 | 1/1982 | Japan . |
| 57-4259 | 1/1982 | Japan . |
| 57-4260 | 1/1982 | Japan . |
| 57-34849 | 2/1982 | Japan . |
| 57-12621 | 3/1982 | Japan . |
| 57-29786 | 6/1982 | Japan . |
| 57-103723 | 6/1982 | Japan . |
| 57-45185 | 9/1982 | Japan . |
| 58-9127 | 1/1983 | Japan . |
| 58-36553 | 3/1983 | Japan . |
| 58-500973 | 6/1983 | Japan . |
| 58-98913 | 7/1983 | Japan . |
| 58-98914 | 7/1983 | Japan . |
| 58-98915 | 7/1983 | Japan . |
| 58-147516 | 10/1983 | Japan . |
| 59-5919 | 1/1984 | Japan . |

(List continue on next page.)

OTHER PUBLICATIONS

Photograph of Petal Soft ® tampon applicator.

Primary Examiner—C. Fred Rosenbaum
Assistant Examiner—Sharon Finkel
Attorney, Agent, or Firm—Fish & Richardson

[57] ABSTRACT

The ease of vaginal insertion experienced with round-edged petal-format tampon applicators can be achieved without the user comfort problems experienced in existing such application by a tampon applicator which has an expulsion end portion of unique structure. Thus, the invention provides an elongate hollow tampon holder shaped for vaginal insertion and having a tampon expulsion end portion and a plunger mounted in the holder and adapted to expel a tampon through the expulsion end portion from the holder interior. The expulsion end portion comprises a dome-shaped portion having an appreciable substantially central aperture therein and comprising a plurality of contiguous segments defined by a plurality of radial slits extending from said aperture through said dome-shaped portion to the base of the dome but no farther. In some embodiments, the expulsion end portion comprises a weakened region around the periphery of the tampon holder functioning as a preformed hinge.

15 Claims, 1 Drawing Sheet

FOREIGN PATENT DOCUMENTS

| | | |
|---|---|---|
| 59-5920 | 1/1984 | Japan . |
| 59-6053 | 1/1984 | Japan . |
| 823837 | 6/1982 | South Africa . |
| 400471 | 4/1978 | Sweden . |
| 22842 | 10/1982 | Sweden . |
| 22795 | 11/1982 | Sweden . |
| 23553 | 11/1982 | Sweden . |
| 2033754 | 5/1980 | United Kingdom . |
| 2033756 | 5/1980 | United Kingdom . |
| 2060396 | 5/1981 | United Kingdom . |
| 2064327 | 6/1981 | United Kingdom . |
| 2081586 | 2/1982 | United Kingdom . |
| 2120945 | 12/1983 | United Kingdom . |
| 2133695 | 8/1984 | United Kingdom . |

TAMPON APPLICATOR

This is a continuation of copending application Ser. No. 07/484,434 filed on Feb. 16, 1990, abandoned, which is in turn a continuation of application Ser. No. 05/563,977 filed on Dec. 21, 1983 now abandoned.

This invention relates to a new concept in tampon applicators.

Tampon applicators comprising a plurality of telescopically-arranged tubes are known. Such applicators are, however, either blunt ended at the end which is intended for vaginal insertion (the "expulsion end") or, in recent years applicators have been developed which are rounded at that end, having a plurality of separated "petals" which are further spaced upon the expulsion through the end of a tampon. The telescopic tube arrangement permits one tube to be used as a plunger to force the expulsion of the tampon from another tube in which the plunger tube is slidably positioned. Although the petal format is more convenient for vaginal insertion, the prior art structures suffer from a number of disadvantages, the most significant of which is probably the tendency of the expanded petal arrangement (after expulsion of a tampon) to catch or nip tissue and hair. By way of example, a petal-type tampon applicator made from plastics material is known in which the rounded tampon expulsion end is constituted by a number of separated petals integrally formed with the remainder of the upper part of the tampon applicator. The petals each come to a point so that the rounded end, before expulsion of a tampon, is closed and has the appearance in end-on view of a circle split into a number of segments. Unfortunately, the petals of this structure have a tendency to nip or catch tissue or hair therebetween when the applicator is in use which tendency is exacerbated by the petals readily springing back to the original configuration after expulsion of a tampon. Existing long petal arrangements also exhibit a problem which arises from the less stable expulsion end configuration produced by long petals. The resulting less stable formed end may produce user discomfort because of the increased risk of the petals being bent back during vaginal insertion.

The present invention aims to provide a structure with the advantages of petal-type applicators but minimizing the disadvantages noted above.

According to the present invention there is provided a tampon applicator comprising an elongate hollow tampon holder shaped for vaginal insertion and having a tampon expulsion end portion and a plunger mounted in the holder and adapted to expel a tampon through the expulsion end portion from the holder interior, the expulsion end portion comprising a dome-shaped portion, having an appreciable substantially central aperture therein and comprising a plurality of contiguous segments defined by a plurality of radial slits extending from said aperture through said dome-shaped portion to the base of said dome-shaped portion but not beyond.

In some embodiments of the invention, such as those in which the tampon applicator is for use with relatively large tampons and includes a relatively thick-walled tube for holding the tampon, it is highly desirable to form a weakened region around the periphery of the tampon holder, positioned at the base of the dome-shaped portion, as described below. In such an embodiment there is provided a tampon applicator comprising an elongate hollow tampon holder shaped for vaginal insertion and having a tampon expulsion end portion and a plunger mounted in the holder and adapted to expel a tampon through the expulsion end portion from the holder interior, the expulsion end portion comprising a weakened region around the periphery of the tampon holder and a dome-shaped end the base of which dome is defined by the weakened region and the dome having an appreciable substantially central aperture therein and comprising a plurality of contiguous segments defined by a plurality of radial slits extending from the aperture to the weakened region but not beyond.

For tampon applicators wherein the structure of the tampon holder is for smaller tampons and includes a relatively thin-walled tube, it is not essential to include the aforementioned weakened region at the base of the dome-shaped portion.

In the applicators described herein, the dome segments (the petals) preferably have truncated ends (when the aperture is polyhedral). The preferred aperture shape is hexagonal.

It is preferred that the tampon holder be in the form of a tube carrying, as the plunger, an inner tube slidably mounted therein. The wall of the tampon holder tube can be supplied with a plurality of grooves and the plunger tube with external nibs which are adapted to engage the grooves thereby to hold the two tubes in predetermined positions with respect to each other. Such features are described and claimed in British Patent Specification No. 1347029 and U.S. Pat. No. 3,696,812.

In embodiments including the weakened region around the periphery of the tampon holder, this region acts as a preformed hinge for the petals. This region preferably comprises a groove or other thinning of the tampon holder wall. Alternatively, in order to produce the hinge function the weakening can take the form of slots or perforations. In the case of a groove, for example, it is not necessary for the groove to be continuous provided that appreciable reduction of stiffness of the structure at this point is achieved.

In embodiments for use with relatively large tampons wherein the tube for holding the tampon is made of paper, the thickness of the tube wall being greater than 0.018 inch, the use of such a weakened region is highly advantageous. It is preferred that for embodiments in which a weakened region is used, the tube wall thickness be in the range from 0.018 to 0.022 inch.

In embodiments for smaller tampons, in which a paper tube for holding the tampon has a tube wall which is relatively thin, for example, in the range 0.012 to 0.015 inch, it is not essential to include such a weakened region.

It will be appreciated that the "expulsion force", i.e., the force required for tampon expulsion, is very important. A structure having an expulsion force below about 300 grams greatly increases the risk of premature tampon expulsion. On the other hand, the expulsion force must be reasonably low to permit proper functioning. A figure of 350 to 450 grams can be quite acceptable, although the invention is not, of course, restricted to this particular range of force. In tampon holders having the above-mentioned weakened region, it should be such as to achieve a satisfactory compromise between weakening of the petals to achieve an acceptably low expulsion force and weakening the petals to the extent that individual petals may drop off during use.

The dome-shaped end may have, for example, six radial slits therein spaced evenly around the periphery of the tampon holder to provide six petals. The use of four petals only increases the expulsion force whereas a number of petals greater than six results in a less stable configuration and imposes formidable tooling constraints in manufacture In the case of small diameter tampon applicator tubes, a five-petal configuration may be acceptable but, overall, six petals of equal size is the preferred configuration.

With the structure disclosed herein, there is no appreciable gap between the relatively small petals before the expulsion of a tampon from the tampon holder. This, and the presence of a region of reduced stiffness which gives a hinge-like function reducing the likelihood of the petals springing back too sharply after expulsion of the tampon, minimize the tissue/hair catching problem outlined above. With such "short" petals the risk of petals being deformed or bent during vaginal insertion or failing to close back adequately is kept to a minimum. Even in the "open" configuration the petal structure transverse dimension is smaller and the gaps between petals are at minimum.

The tampon applicator of the present invention may be fabricated from any material used in the art including, inter alia, cardboard, card, paper and plastics material. Paper (with an outer water-proof, e.g., wax, coating) is preferred having regard to its biodegradability (flushability).

Conventional tampons may be used in the applicator of the present invention, such tampons being usually cylindrical in format and comprised of highly absorbent material. The tampon may have a rounded end to match the dome-shaped end and facilitate expulsion.

The invention will now be further described and illustrated by reference to the accompanying drawings, in which.

Figure 1:
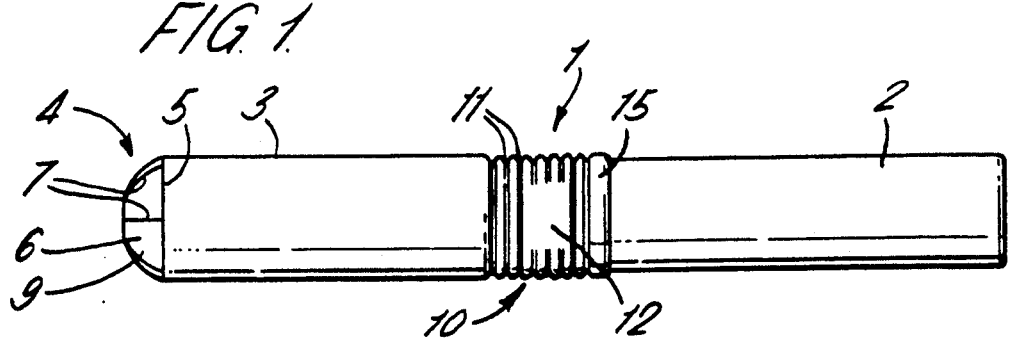
FIG. 1 shows a side view of a tampon applicator in accordance with the invention and having a substantially central aperture.

In FIG. 1, a tampon applicator generally designated 1 comprises an inner tube 2 and an outer tube 3. Outer tube 3 is designed to store a conventional tampon (not shown) within its hollow interior (not shown). At one end of outer tube 3 is an expulsion end portion generally designated 4 which comprises a preformed hinge or groove 5 extending around the periphery of tube 3 (which although shown as continuous in the drawings need not necessarily be so) and a dome-shaped end 6 having a number of radial slits 7 therein extending from a central aperture 8 (more clearly seen in FIG. 3) to the groove 5. Slits 7 define therebetween truncated petals 9.

At the end of tube 3 opposite to the expulsion end portion 4 is a grooved section 10. The grooves 11 constituting this section need not all necessarily extend completely around the periphery of tube 3. In fact, a space 2 may be provided for matter of a Trademark character, by way of example.

Figure 2:
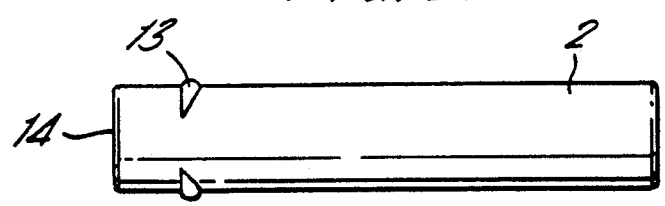
FIG. 2 shows the plunger inner tube of the applicator of FIG. 1.

In FIG. 2, it can be seen that tube 2 has nibs 13 arranged on the periphery thereof close to the end 14 of tube 2 which fits within tube 3. Nibs 13 are adapted to engage with grooves 11 on the inside surface (not shown) of tube 3 thereby providing a number of possible predetermined relative positions for tubes 2 and 3. Grooves 11 and nibs 13 prevent tube 2 from too easily being pushed into tube 3 (resulting in premature opening of the petals) should the applicator 1 be mishandled before use thereof, and also permit the size of the space (not shown) available within tube 3 for receiving a tampon to be selected depending upon tampon size. If extra absorbency is required a longer tampon may be employed and tube 2 may be positioned in tube 3 with nibs 13 engaged in the groove 11 which is furthest from the expulsion end portion 4. A smaller absorbency tampon may be shorter and tube 2 would then be held further into tube 3 with nibs 13 engaging a groove 11 nearer expulsion end portion 4.

The use of small petals 9 which have no appreciable gaps therebetween and which are truncated so as to provide an appreciable aperture 8 and the groove 5 at the base of the petals 9 provides a structure which has ease of vaginal insertion and which minimizes user comfort problems. Absence of inter-petal gaps and use of a truncated petal shape minimizes tissue/hair catching problems, and, although the petals 9 tend to return to a "closed" configuration after tampon expulsion, they do not do so too rapidly as a result of the reduced stiffness provided in the structure by groove 5. It will also be appreciated that if, for example, petals 9 were longer and extended back into the cylindrical portion of tube 3 and groove 5 was positioned further back and not immediately around the base of the curved, dome-shaped portion, the more extended petal size would increase the risk of deformation of petals upon vaginal insertion. A petal arrangement extending throughout the curved end configuration only is important.

Figure 3:
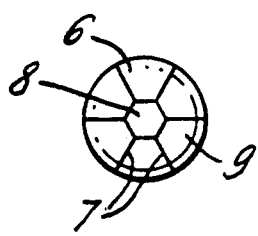
FIG. 3 shows an end-on view of the domeshaped expulsion end of the applicator of FIG. 1.

In FIGS. 1 and 3 it can be seen that the truncated petals 9 comprise a plurality of contiguous smooth-surfaced segments, the outer surface of each of the petals 9 being smooth and free from ridges or valleys in any direction. The tampon applicator described herein is an economical design and provides a product which is convenient and satisfactory from the standpoint of the user.

In use, a tampon (not shown) is contained within tube 3. After insertion of tube 3 through the vagina, the tampon is expelled from the tube by pressing tube 2 into tube 3 manually. The tampon is then expelled by this plunger-like action through expulsion end portion 4 by forcing apart petals 9. Aperture 8 reduces the expulsion force which is required. Once the tampon has been completely expelled through the expulsion end portion 4, the small size petals 9 do not show a tendency to flare unduly and the absence of space between the petals in the unused configuration shape further minimizes the risk of hurt to the user.

In a typical tampon applicator made from laminated paper in accordance with the present invention and as shown in FIG. 1, the length of tube 2 may be 3"±0.005" and the length of tube 3 may be 2⅜"±0.005". Tube diameters may be varied to accommodate different absorbency tampons according to the knowledge of the skilled man. The distance from end 4 and tube 2 to nibs 13 may be typically nine sixteenths of an inch and the ungrooved annular section 15 at the proximate end of tube 3 may be typically one eighth of an inch deep.

Where the aperture 8 is in the shape of a hexagon, each side thereof being of equal length, it is preferable that the size of the aperture be such that the length of a side of the hexagonal aperture be at least 0.05 inch and no greater than 0.15 inch.

As previously explained, in embodiments for smaller tampons in which a paper tube for holding the tampon has a relatively thin wall, it is not essential to include any weakened region such as the groove 5 at the base of the dome-shaped portion of the tampon holder, provided there is an acceptable expulsion force so as to cause proper operation of the applicator.

Figure 4:
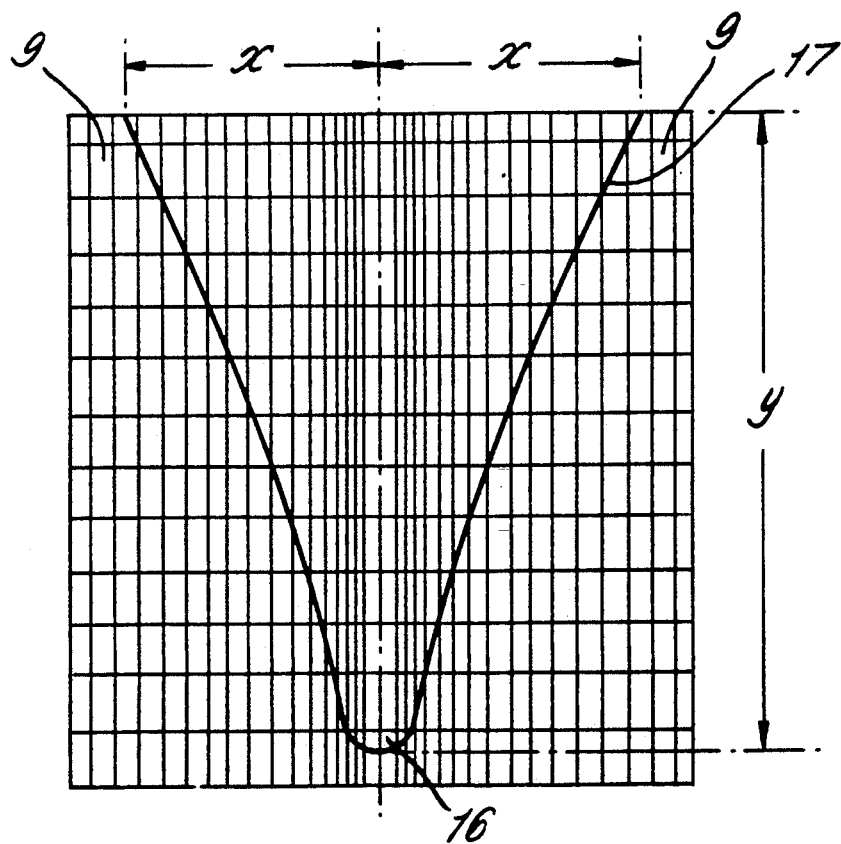
FIG. 4 shows a curve from which a blank may be derived which may be used to produce the expulsion end of an applicator as shown in FIG. 1.

In FIG. 4 is shown a partial section of the shape for a cutout section of the tube 3 which can be folded to provide the dome-shaped structure shown for the expulsion end portion 4 in FIG. 1. The shape and dimensions are chosen carefully in accordance with the knowledge of the skilled man to enable folding to be achieved to provide the unique structure shown in FIGS. 1 to 3. Below, in the Table are set out appropriate dimensions for the dome-shaped end of a tampon applicator in accordance with the present invention taken along axes X and Y shown in FIG. 4. The figures quoted are in inches but, whatever the units, the X/Y ratio at any point on the curve 17 plotted should, of course, be the same. The width of the base 16 of the outline curve 17 of petals 9 is the smallest possible dimension which is practical from a tooling point of view and is about 0.015 inches, i.e., the radius of the base 16 of the curve 17 (the value of X) is 0.0075 inches. This dimension effectively disappears upon folding leaving only slits 7 between petals 9. The shape of the curve 17 is selected to provide the petal structure illustrated in FIGS. 1 to 3 and also avoids the use of surplus material which might provide folds or wrinkles in a folded tube 3 made from a cutout having a different shape.

TABLE

| X | Y |
| --- | --- |
| 0 | 0 |
| .0075 | .0075 |
| .0076 | .0141 |
| .0082 | .0282 |
| .0090 | .0423 |
| .0102 | .0564 |
| .0118 | .0705 |
| .0137 | .0845 |
| .0159 | .0986 |
| .0185 | .1127 |
| .0213 | .1268 |
| .0245 | .1409 |
| .0279 | .1549 |
| .0316 | .1690 |
| .0356 | .1832 |
| .0399 | .1973 |
| .0444 | .2113 |
| .0492 | .2255 |
| .0541 | .2395 |
| .0593 | .2536 |
| .0647 | .2677 |
| .0703 | .2818 |
| .0760 | .2959 |
| .0819 | .3099 |
| .0879 | .3240 |
| .0942 | .332 |

The present tampon applicator outer tubes 3 may be formed, after cutting the desired petal shapes, to the final desired expulsion end shape using a heated mandrel and die. It is preferred, in producing a groove 5 to serve as the preformed hinge (weakened region) at the petal base, to use a mandrel having a groove therein so that as the groove 5 is formed by outside tool action on tube 3 some of the material from which tube 3 is made, e.g., paper, is displaced into the mandrel groove. The resulting groove 5 is when formed partially from such displaced paper.

In the following description comparative tests with respect to various expulsion end structures are given including data on both a conventional bluntended, open-ended tampon applicator and on petal configuration applicator of various types. The same paper material was used to fabricate the tampon holders in each case.

1) Expulsion force for existing blunt, open-ended tampon holder tubes.

Statistical mean for 59 tests=177.37 grams.

Standard deviation=36.4 grams.

2) Petal-type tubes manufactured incorporating 0.015" wide slots at root of petal form giving petal form depth of ⅜"—"long" petal type—no tube groove 5.

Expulsion force in grams—results based upon 25 tests.

Mean 352 Standard deviation 32.

3) Petal-type tubes manufactured with shortened petal form depth of 0.340" but no tube groove 5.

Expulsion force in grams—results based upon 25 tests.

Mean 855. Standard deviation 56.4.

Expulsion forces unacceptably high.

4) Petal-type tubes manufactured with shortened petal form of 0.340" and petal relief groove 0.005" deep in forming mandrel to attempt to form a tube groove 5.

Result, unsatisfactory, petal base cut through.

5) Petal-type tubes manufactured with shortened petal form of 0.340" and petal relief groove 0.010" deep in forming mandrel to form a tube groove 5.

Expulsion force in grams—results based upon 25 tests.

Mean 353. Standard deviation 37.7.

Result unsatisfactory, considerable splitting at base upon testing (see below).

6) Petal-type tubes manufactured with shortened petal form of 0.340" and petal relief groove 0.015" deep in forming mandrel to form a tube groove 5.

Expulsion force in grams—results based upon 25 tests.

Mean 414. Standard deviation 46.3.

Result unsatisfactory slight splitting at petal base upon testing (see below).

7) Petal-type tubes manufactured with shortened petal form of 0.340" and petal relief groove 0.017" deep in forming mandrel to form tube groove 5.

Expulsion force in grams—results based upon 25 tests.

Mean 420. Standard deviation 46.2.

Results satisfactory, no petal failure after 50 petal reforms and 50 tampon expulsions (for testing method see below).

Where indicated above, tests were performed to ascertain whether a number of petal reforms and tampon expulsions caused cracks, fractures or splitting in the petal base. In each case, the test consisted of pushing a single original inner tube 2 through the single original formed outer tube 3 after multiple reforming. Each tube 3 was originally cut with six petals and formed using a heated mandrel and die, both at 100° C. The inner tube 2 was pushed through the petals and the petals examined for cracking or fracture. The same outer tube 3 was reformed using the heated die and mandrel, the inner tube 2 assembled and pushed through the petals which were examined again for cracking or fracture. This sequence is repeated, e.g., up to 100 times.

We claim:

1. A tampon applicator comprising an elongate hollow tampon holder shaped for vaginal insertion and having a tampon expulsion end portion and a plunger mounted in the holder and adapted to expel a tampon through the expulsion end portion from the holder interior, the expulsion end portion comprising a dome-shaped portion, having an appreciable substantially central aperture therein and comprising a plurality of substantially smooth contiguous segments defined by a plurality of radial slits extending from said aperture through said dome-shaped portion to the base of said dome-shaped portion but not beyond, the tampon holder further comprising a weakened region around its periphery positioned at the base of said dome-shaped portion, said weakened region comprising a continuous or discontinuous groove, slots or perforations.

2. An applicator as claimed in claim 1, wherein the segments have truncated ends, the aperture being in the shape of a polygon.

3. An applicator as claimed in claim 1, wherein the segments have truncated ends, the aperture being hexagonal.

4. An applicator as claimed in claim 1, wherein the tampon holder is in the form of a tube carrying, as a plunger, an inner tube slidably mounted therein.

5. An applicator as claimed in claim 1, wherein there are six of said slits equally spaced around the dome-shaped portion.

6. An applicator as claimed in claim 1 which has been fabricated from paper.

7. An applicator as claimed in claim 1 wherein the tampon holder has been fabricated from paper provided with a waterproof, oil and grease resistant surface.

8. A combination of an applicator as claimed in claim 1 and a tampon contained in the tampon holder interior, which tampon has a rounded end shaped to match the dome-shaped end and facilitate its expulsion from the applicator.

9. A tampon applicator as claimed in claim 1, wherein said aperture is in the shape of a hexagon of such size that the length of each side thereof is in the range from 0.05 to 0.15 inch.

10. A tampon applicator comprising an elongate hollow tampon holder shaped for vaginal insertion and having a tampon expulsion end portion and a plunger mounted in the holder and adapted to expel a tampon through the expulsion end portion from the holder interior, the expulsion end portion comprising a dome-shaped portion, having an appreciable substantially central aperture therein and comprising a plurality of contiguous segments defined by a plurality of radial slits extending from said aperture through said dome-shaped portion to the base of said dome-shaped portion but not beyond, at least the major portion of the dome-shaped portion of the tampon holder having substantially the same thickness as at least the major portion of the remainder of the tampon holder, wherein said tampon holder comprises a weakened region around its periphery positioned at the base of said dome-shaped portion.

11. An applicator as claimed in claim 10, wherein the segments have truncated ends, the aperture being in the shape of a polygon.

12. An applicator as claimed in claim 10, wherein said weakened region comprises a continuous or discontinuous groove, slots or perforations.

13. An applicator as claimed in claim 10, wherein the segments have truncated ends, the aperture being in the shape of a hexagon.

14. An applicator as claimed in claim 13, wherein the length of each side of the hexagon is in the range of from 0.05 to 0.15 inch.

15. An applicator as claimed in claim 14, which has been fabricated from paper.

* * * * *